| United States Patent [19] | | | [11] | 3,968,133 |
|---|---|---|---|---|
| Knifton | | | [45] | July 6, 1976 |

[54] CARBOXYLATION PROCESS FOR PREPARING LINEAR FATTY ACIDS OR ESTERS

[75] Inventor: John F. Knifton, Poughquag, N.Y.

[73] Assignee: Texaco Inc., New York, N.Y.

[22] Filed: Nov. 25, 1974

[21] Appl. No.: 526,867

[52] U.S. Cl............... 260/410.9 R; 260/413; 260/497 A; 260/488 K; 260/491; 260/532; 260/533 A
[51] Int. Cl.$^2$.................................. C11C 3/02
[58] Field of Search......... 260/410.9 R, 413, 497 A, 260/488 K, 491, 532, 533 A

[56] References Cited
UNITED STATES PATENTS

| 3,437,676 | 4/1969 | Kutepow | 260/410.9 R |
|---|---|---|---|
| 3,530,155 | 9/1970 | Fenton | 260/410.9 R |
| 3,530,168 | 9/1970 | Biale | 260/410.9 R |
| 3,657,368 | 4/1972 | Parshall | 260/410.9 R |
| 3,700,706 | 10/1972 | Butter | 260/410.9 R |
| 3,723,486 | 3/1973 | Kajimoto | 260/410.9 R |
| 3,776,929 | 12/1973 | Mrowca | 260/410.9 R |
| 3,819,669 | 6/1974 | Knifton | 260/410.9 R |
| 3,832,391 | 8/1974 | Parshall | 260/410.9 R |

*Primary Examiner*—Patrick P. Garvin
*Assistant Examiner*—John F. Niebling
*Attorney, Agent, or Firm*—T. H. Whaley; C. G. Ries; Bernard Marlowe

[57] ABSTRACT

This invention concerns a process for preparing linear fatty (carboxylic) acids and esters from the reaction of olefins, alcohols (or water) and carbon monoxide. The process is catalyzed by catalytic amounts of dispersions of ligand-stabilized, palladium(II) halide complexes, in quaternary ammonium, phosphonium or arsonium salts of trihalostannate(II) or trihalogermanate(II). These empirically selected palladium catalysts can be recycled with fresh olefin feed several times before substantial loss of catalytic activity is encountered.

6 Claims, No Drawings

CARBOXYLATION PROCESS FOR PREPARING LINEAR FATTY ACIDS OR ESTERS

STATEMENT OF INVENTION

This invention relates to the catalytic conversion of alpha-olefins to linear fatty acids or esters.

More particularly, this invention concerns the carboxylation of alpha-olefins with carbon monoxide in the presence of hydroxyl-containing co-reactant, under moderate conditions of temperature and pressure, using dispersions of certain ligand-stabilized palladium-(II) halides in quaternary ammonium, phosphonium and/or arsonium salts of trihalostannate (II) or trihalogermanate(II).

Carboxylation, as used througout this disclosure and claims, refers to the process of preparing saturated, preferably linear carboxylic acids or their esters from alpha-olefin substrates. Linear paraffinic carboyxlic esters are of the type: RCOOR', wherein R is a saturated alkyl radical containing 3 to 40 carbon atoms, wherein R' is an aliphatic or aromatic radical.

BACKGROUND OF THE INVENTION

Carboxylic acids are characterized by the presence of one of more carboxyl groups in an organic molecule. The acids are usually written as RCOOH. The hydrogen atom of this group may be displaced and appear as a hydronium ion thereby justifying by theory the term acid.

Saturated linear carboxylic acids and their esters may be prepared by a large number of general procedures such as the oxidation of primary alcohols or aldehdyes, the catalytic hydrolysis of nitriles, the reaction of Grignard reagents with carbon dioxide as well as by several special procedures for specific acids including fermentation, the acetoacetic ester synthesis, the malonic ester synthesis and the Reformatsky reaction.

In recent years, with the availability of large quantities of alpha-olefins from wax cracking at relatively low costs, alpha-olefins have been considered as starting materials for fatty acid production.

The carboxylation of olefins in the presence of metal carbonyls or carbonyl precursors to produce carboxylic acids or esters is old in the literature, originally having been developed by Reppe* and his coworkers. However, the nickel and iron salts or carbonyl precursors suffer from some major drawbacks. These drawbacks include the high toxicity of the carbonyl type reagents, the production of a variety of undesirable side products due to polymerization, isomerization and reduction of the olefin substrates and most importantly, the reaction results in the production of large quantities of branched isomers in addition to the desired linear fatty acid product.

*This work is reviewed by C. W. Bird, Rev.62,283 (1962)

Recently, it has been shown that the production of polymeric, isomeric and reduced products can be avoided through the use of alternative homogeneous catalyst systems which are active under mild reaction conditions and which give good yields and selectivity to the desired linear fatty acids or esters. These catalyst systems consist of ligand-stabilized platinum(II) and palladium(II) halide complexes in combination with Group IVB metal halides. They are exemplified by:

$PtCl_2[As(C_6H_5)_3]_2$-$SnCl_2$ (U.S. Pat. No. 3,819,669) and $PdCl_2[P(C_6H_5)_3]_2$-$SnCl_2$ (U.S. Pat. No. 3,700,706).

While these homogeneous catalysts are a vast improvement over the more easily poisoned and less selective heterogeneous catalysts, and the widely used highly toxic metal carbonyls such as nickel, cobalt and iron cabonyls. They also have certain drawbacks. These include difficulties in maintaining high conversions, high selectivities and high yields upon recycling the catalyst, due to catalyst degradation, and the problems of mechanical losses, and further catalysts decomposition, during the separation of the carboxylated products from the homogeneous catalysts and solvents. Catalyst instability is a particular problem with the less thermally stable palladium-containing homogeneous catalysts.

CLOSEST PRIOR ART AND DISTINCTIONS OF THIS INVENTION OVER SAID ART

The closest prior art that the applicant is aware of is U.S. Pat. No. 3,657,368 (G. W. Parshall). This patent describes the use of certain transition metal halides in combination with molten quaternary ammonium or phosphonium trihalostannate(II) and trihalogermanate(II) salts as catalysts for the carboxylation, hydroformulation, hydrogenation and isomerization of olefins, and the hydrogenation of nitriles.

The following differences of substance are believed to patentably distinguish applicant's claimed invention from the disclosure of Parshall. 1. While Parshall ostensibly discloses platinum and palladium halides dispersed in molten quaternary ammonium or phosphonium trihalostannate(II) and trihalogermanate(II) salts for the catalytic carboxylation of alpha-olefins, no palladium-containing catalysts are specifically named or described by Parshall, much less employed.

The sole "disclosure" can be found in Column 2, lines 21–32, more specifically, lines 22–25, ". . . . (A) at least 0.05 weight percent of a chloride, bromide or iodide-containing salt of a metal having an atomic number of 22–28, 40–46 or 72–79, and (B) . . . "

The following reasons are evidenciary of why the Parshall patent does not constitute a bona fide disclosure of the use of the analogous palladium catalysts even to those skilled in the art:

1. While it is known that palladium has an atomic number of 46 and Column 2, lines 21 to 32 states that metal halides of 40–46 are useful as catalytic entities, this disclosure is sufficient to characterize the specific components of active palladium containing catalysts in order to reject applicant's specifically claimed catalysts on Parshall.

2. A further reason why this type of "tour de force" disclosure is a meaningless teaching to reject applicant's claims is that it is well documented in the patent literature* that catalysis is a most unpredictable art and does not lend itself to broad generic disclosures supported by only a few isolated species, particularly when such broad disclosures can encompass many catalyst species which are not available for testing or are even unknown. For instance, virtually every component of a multi-component homogeneous platinum(II) or palladium(II) catalyst system, such as the noble metal employed, the nature of the halide salt, the presence of absence of stabilizing ligands, the structure of the molten quaternary ammonium or phosphonium trihlaostannate(II) or trihalogermanate(II) salts present can each affect not only the degree of conversion, selectivity and yield but, in some cases, even the operability.

These statements are confirmed by the data in Tables 1 and 2.

In re Grant, 134 U.S.P.Q. 248, among others.

3. Many of the catalyst compositions disclosed generally in U.S. Pat. No. 3,657,368 (See Column 2, lines 21–32) and specifically (See Column 2, lines 38–45) for the carbonylation of olefins have been found inactive by us for the carboxylation of α-olefins, as exemplified by 1-octene, to linear carboxylic acid esters, such as vinyl nonanoate under experimental conditions where the preferred ligand-stabilized palladium(II) catalysts, such as $[(C_2H_5)_4N]SnCl_3\text{-}PdCl_2(P(C_6H_5)_3)_2$ show good activity. This is confirmed by the data in Table 2.

4. When the closest platinum-containing catalyst disclosed by Parshall for the carboxylation of alpha olefins;

$10[(C_2H_5)_4N[SnCl_3]\text{-}PtCl_2[P(C_6H_5)_3]_2$ is run side by side with the analogous palladium catalyst utilized by applicant, viz.

$10[(C_2H_5)_4N][SnCl_3]\text{-}PdCl_2[P(C_6H_5)_3]_2$ under identical reaction conditions, to carboxylate the same alpha-olefin, an improvement in conversion of more than 25-fold and an increase in yield of over 70-fold is noted and the purity of product is even higher with the palladium catalyst. This statement is confirmed by the data in Table 1. Similarly, the platinum-(II) catalyst $[(C_2H_5)_4N][SnCl_3]\text{-}PtCl_2$ disclosed by Parshall in Column 10 Example 27 of the same patent, gives only trace amounts of carboxylic acid ester under the mild conditions preferred for the palladium catalysts disclosed herein. This statement is confirmed by the data in Table 2.

5. In addition to differences in the choice of noble metal employed for the carboxylation reaction (e.g. palladium catalysts claimed here by applicant versus the platinum catalysts taught by Parshall) the applicant has also found that improved yields of fatty acid esters are generally obtained using molar ratios of quaternary tin(II) or germanium(II) salt component to noble metal component of between 5 to 10 rather than the ratios of 100 or more practiced by Parshall. Evidence for this statement may be found in Tables 1 and 3.

6. Most important from a commercialization standpoint, the empirically selected palladium-containing catalyst complexes claimed by the applicant show excellent capability for recycling compared to the analogous platinum catalysts disclosed by Parshall. This is proven when the reaction mixture containing fresh α-olefin, alcohol carbon monoxide are run in a continuous process for producing fatty acid ester products without exhibiting substantial loss in yield or selectivity. This unexpected property greatly reduces operating costs by cutting down regeneration of the palladium catalysts and so far as is known is not reported in the literature. Evidentiary of this recycle capability of the $[(C_2H_5)_4N]SnCl_3\text{-}PdCl_2[P(C_6H_5)_3]_2$ and $[(C_2H_5)_4N]SnCl_3\text{-}PdCl_2[P(p\text{-}CH_3.C_6H_4)_3]_2$ catalysts may be found in Tables 4 to 6. The following palladium catalyst compositions have been found to be active for the carboxylation of α-olefins to linear fatty acids or esters:

a. $10\ [(C_2H_5)_4N][SnCl_3]\text{-}PdCl_2[P(p\text{-}CH_3.C_6H_4)_3]_2$
b. $10\ [C_2H_5(_4N][SnCl_3]\text{-}PdCl_2[P(C_6H_5)_3]_2$
c. $5\ [ClCH_2(C_6H_5)_3P][SnCl_3]\text{-}PdCl_2[P(C_6H_5)_3]_2$
d. $10\ [(n\text{-}C_4H_9)_4N](SnCl_3]\text{-}PdCl_2[P(C_6H_5)_3]_2$
e. $5\ [(C_6H_5)_4As](SnCl_3]\text{-}PdCl_2[P(C_6H_5)_3]_2$
f. $5\ [(C_7H_{15})_4N][SnCl_3]\text{-}PdCl_2[P(C_6H_5)_3]_2$
g. $10\ [(C_2H_5)_4N][SnCl_3]\text{-}PdCl_2[P(p\text{-}CH_3O.C_6H_4)_3]_2$
h. $10\ [(C_2H_5)_4N][SnCl_3]\text{-}PdCl_2[P(CH_3)_2C_6H_5]_2$
i. $5\ [(C_2H_5)_4N][GeCl_3]\text{-}PdCl_2[P(C_6H_5)_3]_2$
j. $5\ [(C_2H_5)_4N][GeCl_3]\text{-}PdCl_2[As(C_6H_5)_3]_2$
k. $10\ [(CH_3)_4N][SnCl_3]\text{-}PdCl_2[P(C_6H_5)_3]_2$
l. $10\ [(C_2H_5)_4N][SnCl_3]\text{-}PdCl_2[As(C_6H_5)_3]_2$ Of the 12 catalyst compositions described supra, the palladium calalyst compositions (a) through (j) (inclusive) have been found to show superior performances compared to analogous platinum catalysts disclosed by Parshall for the carboxylation of α-olefins. Comparative data are summarized in Tables 1 and 2 for the typical synthesis of ethyl nonanoate from 1-octene under standard experimental conditions.

More generally it is anticipated that the palladium catalysts of this invention should consist of ligand-stabilized palladium(II) halide complexes dispersed in quaternary ammonium, phosphonium and arsonium salts of trihalostannate(II) and trihalogermanate(II) wherein:

a. The stabilizing ligands contain one or more phosphorous or arsenic donor atoms bonded to various alkyl, aryl or substituted aryl groups.
b. The palladium halide salt is palladium chloride or bromide, and
c. The quaternary ammonium, phosphonium or arsonium salts contain alkyl, cycloalkyl, aryl, substituted aryl, substituted alkyl and mixed alkaryl groups each having 1 to 12 carbon atoms, or mixtures thereof.

B. General Description and Discussion for the Carboxylation of Olefins

In the broadest process embodiment envisioned, the substrate olefin would be contacted with a catalytic amount of a dispersion of ligand-stabilized palladium(II) halide complex in quaternary ammonium, phosphonium or arsonium trihalostannate(II) or trihalogermanate(II) salt, in the presence of sufficient quantity of hydroxylated coreactant and carbon monoxide to satisfy the stoichiometry of the carboxylation reaction, at elevated temperatures and under superatmospheric pressure for a time sufficient to form the desired linear fatty acid or ester products.

Ordinarily, the catalyst is prepared in situ, in the absence of oxygen or oxidizing agents, preferably in an inert environmenrt such as is afforded by a nitrogen or other inert gas atmosphere, in a reactor which is equipped for pressurized reactions at elevated temperatures. While it is generally less convenient, the catalyst can be preformed, and contacted with the degassed olefin to be carboxylated, under said inert purge and hydroxylated coreactant, pressurized with carbon monoxide, sealed and heated under the superatmospheric pressure for the required time, cooled, vented off, and the product mixture recovered for work-up.

Generally, the quaternary ammonium, phosphonium or arsonium trihalostannate(II) or trihalogermanate(II) salt, and the ligand-stabilized palladium(II) dihalide are contacted with a degassed sample of olefin (to be carboxylated) and alcohol co-reactant under an inert gas purge and are transferred to a reactor which is deoxygenated, pressurized with carbon monoxide and heated until analysis or experience has shown that the carboxylation reaction is substantially complete.

C. Work-up of Carboxylated Reaction Mixture

Two work-up procedures have been practiced. In one case the product ester may be recovered by a solvent extraction technique as follows:

1. a. The crude liquid ester product is separated from the product mixture by filtration, centrifugation, etc.
   b. The crude ester is subject to flash distillation under reduced pressure to remove unreacted olefin and excess alcohol,
   c. The partially purified ester is extracted with a non-polar solvent, such as petroleum ether, to precipitate dissolved melted components,
   d. The non-polar extract is distilled to recover residual ester, and
   e. The recovered melt catalyst from steps (a) and (c) is combined and recycled with additional olefin and alcohol.

An alternative recovery procedure is recovery of the product ester by a vacuum distillation technique, as follows:

2. a. The crude liquid ester product is separated from the product mixture by filtration etc.
   b. The crude liquid product of (a) is subject to distillation under reduced pressure to strip off unreacted octene and alcohol,
   c. The partially purified ester is subject to fractional distillation in vacuo,
   d. The recovered residual melt catalyst from steps (a) and (c) is combined, and recycled with additional olefin and alcohol.

D. Molar Ratio of Tin or Germanium Halide to palladium(II) Halide

As can be seen from the data of Tables 1 and 3, while the ratio of tin or germanium to palladium in the catalyst is not critical for operability, consistently higher conversions, yields and selectivities can be obtained using molar ratios of tin (or germanium) to palladium ranging from 1 to 100 mole Sn(Ge) per mole of Pd. However, inasmuch as the highest conversions, selectivities and yields of ester are produced at molar ratios of tin (or germanium) ranging from 5 to 10 mole per mole of palladium, this represents the preferred molar range of tin or germanium to palladium. Interestingly enough, the Parshall patent discloses much higher molar ratios of tin to platinum, that is, the disclosed catalysts contain molar ranges of tin to platinum of 100:1 or higher.

E. Molar Ratio of Calalyst to Olefin Substrate

Experimental work indicates that a molar ratio of 10 to 500 moles of olefin per mole of the palladium catalyst complex can be employed where alpha olefins as typified by 1-octene, are used as the substrate. Much lower ratios (i.e. less than 10 moles of olefin substrate per mole of palladium) are not harmful but are economically unattractive. For this reason, as documented by Table 3, ranges from 10 to 500 moles of olefin per mole of palladium(II) catalyst composition are preferred.

F. Experimental Conditions Required for Carboxylation

The rates of carboxylation of typical $\alpha$-olefins are dependent upon the temperature, the pressure of carbon monoxide, and the concentrations and choices of palladium catalyst and alpha-olefin employed. Again using 1-octene as a typical alpha-olefin, and 10 $[(C_2H_5)_4N]SnCl_3\text{-}PdCl_2[P(C_6H_5)_3]_2$ as a representative catalyst, an operable temperature range is at least 25° to 120°C or more.

Superatmospheric pressures of at least 100 psig are required for substantial conversion of the alpha olefin to the linear fatty (carboxylic) acid or ester.

The time of reaction may vary from a few minutes to twelve hours or more. Generally substantial conversions of the $\alpha$-olefin can almost always be accomplished within 2 to 8 hours. Table 3 provides the supporting experimental data which establish these ranges in experimental conditions.

G. Alpha (60) Olefins as Substrates

Alpha-olefins ranging in carbon content from three (3) up to forty (40) carbon atoms can be employed. Illustrative linear alpha olefin substrates include 1-propene, 1-butene, 1-pentene, 1-hexene, 1-heptene, 1-octene, 1-nonene, 1-decene, 1-undecene, 1-dodecene, 1-tetradecene as well as their higher homologues such as 1-heptadecene, 1-octadecene, 1-eicosene, tricosene, 1-pentacosene, etc. Branched alpha-olefins can also be carboxylated. Illustrative branched alpha-olefin substrates are 3-methyl-1-pentene, 4-methyl-1-pentene, 4,4-dimetyl-1-pentene and 3,6,9-triethyl-1-decene. These olefin substrates may be utilized neat or in conjunction with one of more inert background solvents such as octanes and the like. The alpha-olefins can be in the form of single, discrete compounds or in the form of mixtures of olefins. In the latter case these comprise mixtures of $C_3$ to $C_{30}$ carbon containing alpha olefins. Usually these mixtures have a spread of from 4 to 8 carbon atoms. Because of their relatively low cost, mixtures of alpha-olefins ranging in carbon content from $C_5$ to $C_{10}$ and upwards are favored substrates for carboxylation wherein the ligand-stabilized palladium-(II) halides dispersed in quaternary ammonium trihalostannate(II) or trihalogermanate(II) salts are employed as carboxylation catalysts at sufficiently elevated temperatures and pressures.

H. Hydroxyl-containing co-reactants

This terms as employed throughout this application refers to water and other hydroxyl-containing reactants which contain at least one hydroxyl group which is sufficiently labile during the reaction conditions of the carboxylation reaction to produce the desired carboxylated product. The physical form of the hydroxyl-containing reactant is not important, that is it can be a liquid or solid. The main other criteria is that it is capable of being dispersed or dissolved in the reaction mixture so that the carboxylated product is formed. Illustrative suitable hydroxyl-containing co-reactants include water, primary or secondary alcohols including methanol, ethanol, n-propanol, n-butanol, isopropanol, cyclohexane, n-dodecanol, phenol and substituted phenols, substituted alcohols such as 2-chloroethanol, and polyols including ethylene glycol, propylene glycol, glycerol, sorbitol and the like. To produce the free acid by this process water must be used as the hydroxyl-containing reactant. To produce the esters one or more paraffinic or aromatic alkanols, glycols and/or polyols must be employed as the hydroxyl-containing paraffinic reactant.

The amount of water or hydroxyl-containing paraffinic reactant used is based upon the concentration of the alpha-olefin to be converted to the carboxylate product. For maximum product yields, at least a stoichiometric quantity of "hydroxyl" reactant should be present (as stated above) dependent upon alpha-olefin concentration. This includes water as well as the alcohols, glycols and polyols.

The favored and sole suitable reactant for producing the free acid is water; the favored hydroxyl-containing reactant being the lower alkanols, particularly those containing 1 to 12 carbon atoms.

I. Carbon Monoxide Environment

Insofar as can be determined, the best selectivities and conversions of alpha-olefins to linear fatty acids can be obtained within a reasonable time by using a substantially carbon monoxide gaseous atmosphere. However, particularly in continuous operation, the carbon monoxide may be used in conjunction with from about 0 to 30% by volume of one or more inert gases such as nitrogen, argon, neon and the like without experiencing a substantial decrease in yield and selectivity.

J. Selectivity

Selectivity as described herein is the efficiency in catalyzing a desired carboxylation reaction relative to other undesired carboxylation reactions. In this instance carboxylation to the linear fatty acid or ester derivative is the desired conversion. Selectivity is usually expressed as a percentile and is calculated by determining the amount of linear carboxylated product formed, divided by the total amount of carboxylated products formed and multiplying the quotient obtained by 100.

K. Conversion

Conversion as defined herein is the efficiency in converting the olefin charge to nonolefinic products. Conversion also is expressed as a percentile and is calculated by dividing the amount of olefin consumed during carboxylation by the amount of olefin originally charged and multiplying the quotient by 100.

L. Yield

Yield as defined herein is the efficiency in catalyzing the desired carboxylation reaction relative to other undesired reactions. In this instance carboxylation to fatty acid or ester derivative is the desired conversion. Yield is usually expressed as a percentile, and is calculated by determining the total amount of carboxylated product formed, divided by the amount of alpha-olefin charged and multiplying the quotient obtained by 100.

M. Identification Procedures

Identification procedures, where applicable, are by one or more of the following analytical procedures — gas chromatograph (g.c.) infrared, nuclear magnetic resonance. Unless otherwise specified all percentages are by weight rather than volume and all temperatures are in centigrade rather than fahrenheit.

Having described the inventive process in general terms, the following examples are submitted to supply specific and illustrative embodiments.

EXAMPLE 1

PREPARATION OF ETHYL NONANOATE BY THE CARBOXYLATION OF 1-OCTENE

Part A

To a degassed sample of 1-octene (400 mmole) and ethanol (400 mmole) contained in a reactor equipped for pressurizing, heating, cooling and means of agitation is added under a nitrogen environment, tetraethylammonium trichlorostannate(II) (40 mmole) and bis-(triphenylphosphine) palladium(II) chloride (4.0 mmole). The reactor is sealed, deoxygenated with a purge of nitrogen, and pressurized under carbon monoxide (1500 psig) while heating the agitated mixture between 80° and 95°C for 3–6 hours. At the end of this time the reaction is terminated by discontinuing the flow of carbon monoxide, cooling, and venting the reactor. The crude ester product is filtered, distilled under reduced pressure (30 cm of mercury) to remove unreacted olefin and excess alcohol and fractionally distilled at 2–4 mm of mercury to recover the methyl nonanoates* shown below. Gas chromatographic (G.C.) analysis indicates the following conversion, selectivity and yield expressed in molar percentages.

| | |
|---|---|
| Octene Conversion | 91% |
| Ethyl Nonanoate Selectivity** | 83% |
| Total Yield of Ethyl Nonanoates* | 84% |

*A mixture of ethyl nonanoate with some ethyl 2-methyloctanoate and ethyl 2-ethylheptanoate.
**Calculated from: Total ethyl nonanoate/total ethyl $C_9$ acid ester.

PART B

The procedure of Example 1A is followed substantially as described above, except that in separate runs the ethanol coreactant is substituted by methanol, n-propanol, n-butanol and n-pentanol. In all instances comparable octene conversions and linear nonandate ester selectivitives are obtained.

PART C

Again the procedure of Example 1A is substantially followed, except that the following hydroxyl-containing co-reactants are substituted for ethanol as the hydroxyl-containing co-reactant.

2-chloroethanol,
1-decanol,
ethylene glycol,
propylene glycol,
1-dodecanol,
phenol and
dipropylene glycol.

In all instances comparable conversions of 1-octene to the linear esters are obtained.

EXAMPLES 2 TO 15

THE CARBOXYLATION OF 1-OCTENE TO ETHYL NONANOATE — EFFECT OF VARYING THE PALLADIUM CATALYST COMPOSITION

In these examples the carboxylation of 1-octene is carried out in accordance with the procedure of Example 1A, in the presence of various ligand-stabilized palladium (II) complexes dispersed in quaternary ammonium, phosphonium and arsonium salts of trihalostannate(II) and trihalogermanate(II), under constant temperature, pressure and substrate-to-catalyst molar ratio conditions. As can be seen from the data in Table I, a variety of ligands can e used to stabilize the palladium(II), including ligands with phosphorus and arsenic donor atoms bonded to alkyl, aryl and substituted aryl groupings. Likewise, the quaternary ammonium, phosphonium and arsonium salts may contain nitrogen, phosphorus or arsenic atoms bonded to various alkyl, aryl, substituted aryl or substituted alkyl groups, and mixtures thereof, in combination with both the trichlorostannate(II) and trichlorogermanate(II) anions.

Of the twelve palladium catalyst compositions exemplified in Table I, the best 1-heptene conversions and ethyl nonanoate yields are obtained with the bis(triphenylphosphine)palladium(II) chloride and bis(tri-p-tolylphosphine)palladium(II) chloride complexes dispersed in tetraethylammonium trichlorostannate(II) salt (Examples 2 and 3). Each of the catalyst compositions of Examples 2 through 11 (inclusive) show superior performances compared with the analogous platinum catalyst,

disclosed by Parshall in U.S. Pat. No. 3,657,368, and similar platinum complex compositions. (See Examples 14 and 15)

ation conditions, where the applied Co pressure is 1500 psig (102 atm) versus 400 atm disclosed by Parshall, only trace amounts of ethyl nonanoates were obtained.

TABLE 1

ETHYL NONANOATE SYNTHESIS FROM 1-OCTENE-CATALYST COMPOSITION STUDIES[a]

| EX. | CATALYST-COMPOSITION | OCTENE CONV. (%) | ETHYL $C_9$ SELECTIVITY(%)[c] | ACID ESTER[b] YIELD (MOLE %) |
|---|---|---|---|---|
| 2 | $10[(C_2H_5)_4N][SnCl_3]-PdCl_2[P(p-CH_3.C_6H_4)_3]_2$ | 80 | 85.6 | 87 |
| 3 | $10[(C_2H_5)_4N][SnCl_3]-PdCl_2[P(C_6H_5)_3]_2$ | 83 | 86.3 | 83 |
| 4 | $5[ICH_2(C_6H_5)_3P][SnCl_3]-PdCl_2[P(C_6H_5)_3]_2$ | 70 | 87.3 | 67 |
| 5 | $10[(n-C_4H_9)_4N][SnCl_3]-PdCl_2[P(C_6H_5)_3]_2$ | 66 | 78.8 | 63 |
| 6 | $5[(C_6H_5)_4As][SnCl_3]-PdCl_2[P(C_6H_5)_3]_2$ | 55 | 69.8 | 35 |
| 7 | $5[(C_7H_{15})_4N][SnCl_3]-PdCl_2[P(C_6H_5)_3]_2$ | 22 | 58 | 19 |
| 8 | $10[(C_2H_5)_4N][SnCl_3]-PdCl_2[P(p-CH_3.O.C_6H_4)_3]_2$ | 60 | 85.8 | 48 |
| 9 | $10[(C_2H_5)_4N][SnCl_3]-PdCl_2[(CH_3)_2C_6H_5]_2$ | 35 | 87.4 | 33 |
| 10 | $5[(C_2H_5)_4N][GeCl_3]-PdCl_2[P(C_6H_5)_3]_2$ | 70 | 84.3 | 62 |
| 11 | $5[(C_2H_5)_4N][GeCl_3]-PdCl_2[As(C_6H_5)_3]_2$ | 20 | 85.2 | 15 |
| 12 | $10[(CH_3)_4N][SnCl_3]-PdCl_2[P(C_6H_5)_3]_2$ | 5 | 89.0 | 3.6 |
| 13 | $10[(C_2H_5)_4N][SnCl_3]-PdCl_2[As(C_6H_5)_3]_2$ | 2 | 92.5 | 16 |
| 14 | $10[(C_2H_5)_4N][SnCl_3]-PtCl_2[P(C_6H_5)_3]_2$[d] | 2.7 | 92 | 1 |
| 15 | $10[(C_2H_5)_4N][SnCl_3]-PtCl_2[As(C_6H_5)_3]_2$ | 2 | 88 | 1.1 |

[a]All runs made at: 1500 psig CO; 85°C; 7 hr.[ 1-octene]/[Pd]=100,(1-octene)/(ethanol)=1
[b]Primarily a mixture of ethyl nonanoate with some ethyl 2-methyl octanoate and ethyl 2-ethyl heptanoate
[c]Calculated from: total ethyl nonanoate/total ethyl $C_9$ acid ester
[d]A standard catalyst described by Parshall in U.S.P. 3,657,368

EXAMPLE 16 TO 22

THE CARBOXYLATION OF 1-OCTENE TO ETHYL NONANOATE — EFFECT OF USING OTHER TRANSITION-METAL CATALYST COMPOSITIONS

In these examples, the carboxylation of 1-octene is carried out in accordance with the procedure of Example 1A, but using as catalysts a variety of transistion-metal salts, particularly platinum, nickel, ruthenium, iron, cobalt and molybdenum salts and complexes dispersed in a typical quaternary ammonium salt of trichlorostannate(II), namely N,N,N,N-tetraethylammonium trichlorostannate(II). As can be seen from the data in Table 2, the following catalyst compositions, disclosed previously in U.S. Pat. No. 3,657,368, proved to be inactive for 1-octene carboxylation under the standard experimental conditions employed in Examples 1 to 13 for the active palladium catalysts:

$[(C_2H_5)_4N]SnCl_3-MoCl_5$
$[(C_2H_5)_4N]SnCl_3-CoCl_2$
$[(C_2H_5)_4N]SnCl_3-NiCl_2$
$[(C_2H_5)_4N]SnCl_3-FeCl_2$

It may also be noted that the palladium catalyst in the absence of stabilizing ligands (Example 22) viz.

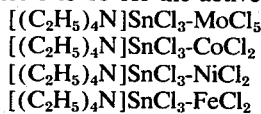
$[(C_2H_5)_4N]SnCl_3-PdCl_2$ yields only trace amounts of nonanoate esters, under conditions where ligand-stabilized palladium(II) catalysts such as exemplified in Examples 1 to 11 give good yields of desired esters.

The preceding data obtained on pages 19 and 20 of this application were run to refute or confirm Parshall's allegation that any of the transition metals having atomic numbers falling within the groups having an atomic number of 22–28, 40 –46 or 72–79 could be used as the catalytic entity in the carboxylation of alpha-olefins. (See Col. 2, lines 21–32). As the above mentioned data of pages 19 and 20 confirm: Molybdenum (atomic number 42) catalysts were inactive for carboxylation, as were ruthenium (Atomic Number 44), cobalt (Atomic Number 27), Iron (Atomic Number 26), nickel (Atomic Number 28) and platinum (Atomic Number 78). Since all of these typical transition metals disclosed by Parshall unexpectedly proved to be completely ineffective as carboxylation catalysts, the alleged broad disclosure of Parshall as set forth in

TABLE 2

ATTEMPTED ETHYL NONANOATE SYNTHESIS FROM 1-OCTENE USING OTHER TRANSITION METAL COMPLEXES[a]

| EXAMPLE | CATALYST COMPOSITION | OCTENE CONV.(%) | ETHYL $C_9$ ACID ESTER YIELD (MOLE %) |
|---|---|---|---|
| 16 | $10 [(C_2H_5)_4N]SnCl_3-K_2PtCl_4$ | 1 | Trace |
| 17 | $10 [(C_2H_5)_4N]SnCl_3-RuCl_2[P(C_6H_5)_3]_3$ | 1 | None |
| 18 | $10 [(C_2H_5)_4N]SnCl_3-CoCl_2$ | 1 | None |
| 19 | $10 [(C_2H_5)_4N]SnCl_3-FeCl_2$ | 1 | None |
| 20 | $10 [(C_2H_5)_4N]SnCl_3-NiCl_2$ | 1 | None |
| 21 | $10 [(C_2H_5)_4N]SnCl_3-MoCl_5$ | 1 | None |
| 22 | $10 [(C_2H_5)_4N]SnCl_3-PdCl_2$ | 1 | Trace |

[a]All runs made at 1500 psig CO, 85°C, 7 hr., [1-octene]/[M]=100, [1-octene]/[ethanol]=1

Similarly, the ligand-stabilized ruthenium(II) complex, $RuCl_2[P(C_6H_5)_3]_2$, gave no acid ester under these conditions (Example 17). The platinum(II) chloride catalyst shown in Example 16, viz.

$[(C_2H_5)_4N]SnCl_3-PtCl_2$
is similar to that disclosed in U.S. Pat. No. 3,657,368, Example 27. However, under our standard carboxylhis patent should not be used to reject applicant's claims drawn to specific palladium (Atomic Number 46) catalyst complexes.

EXAMPLES 23 to 30

THE CARBOXYLATION OF 1-OCTENE TO METHYL NONANOATE — EFFECT OF VARYING THE OPERATING CONDITIONS

In these examples, using the same techniques of Example 1A, together with the same palladium catalyst, $[(C_2H_5)_4N]SnCl_3\text{-}PdCl_2[P(C_6H_5)_3]_2$, and the same $\alpha$-olefin charge, 1-octene, the effect of varying the carboxylation temperature, pressure of CO, and reactant mole ratios has been examined. The results are summarized in Table 3. It is evident from the data that carboxylation of 1-octene to methyl nonanoate may be achieved with this catalyst system over a wide range of conditions, as follows:

a. Molar ratios of tin salt to palladium complex ranging from 5:1 up to 100:1, respectively.
b. Initial molar ratios of $\alpha$-olefin to palladium catalyst ranging from 10:1 up to 500:1.
c. Operating temperatures of 25° to 120°C.
d. Superatmospheric pressures of at least 100 psig of CO.

1. The crude liquid product containing the liquid ester is filtered from the crystalline melt.
2. The crude ester of (1) is flash distilled under reduced pressure (1 cm to 75 cm of mercury) to strip off unreacted octene and methanol.
3. The ester from step (2) is extracted three times with excess petroleum ether to precipitate the dissolved catalyst melt.
4. The ether extract is flash distilled under reduced pressure (1 cm to 75 cm of mercury) to recover methyl nonanoates, and
5. The recovered melt from steps (1) and (3) is combined with additional 1-octene and excess methanol. Table 4 documents the results obtained.

TABLE 4

CARBOXYLATION OF 1-OCTENE TO METHYL NONANOATE - CATALYST RECYCLE STUDY - I[a]

| EXAMPLE | CATALYST CYCLE | OCTENE CONVERSION(%) | LIQUID YIELD(%) | METHYL $C_9$ ACID SELECTIVITY(%)[c] | ESTER YIELD(MOLE %)[d] | ISOLATED ESTER PURITY |
|---|---|---|---|---|---|---|
| 31 | I | 80 | 85 | 86.3 | 85 | 95 |
| 32 | II | 80 | 88 | 86.5 | 81 | 95 |
| 33 | III | 74 | 94 | 89.5 | 72 | 96 |
| 34 | IV | 29 | 96 | 90.6 | 25 | 98 |

[a]Run Conditions: 1500 psig CO; 85°C, 10 hr.; [Sn]/[Pd]=9.6; [1-octene]/[Pd]=92; [Methanol]/[1-octene]=1.9.
[b]A mixture of methyl nonanoate with some methyl 2-methyl octanoate and methyl 2-ethylheptanoate.
[c]Selectivity to linear methyl nonanoate based on total methyl nonanoate/total methyl $C_9$ester.
[d]Yield based on octene charged.

As can be seen from the results presented in Table 4, methyl nonanoate ester yields remain essentially equivalent over the first three cycles of the $[(C_2H_5)_4N]SnCl_3\text{-}PdCl_2[P(C_6H_5)_3]_2$ catalyst, but some deactuation is evident in the 4th cycle. On the other hand, the selectivity to linear methyl nonanoate improves steadily with successive cycling.

In a similar experimental series to Examples 28

TABLE 3

CARBOXYLATION OF 1-OCTENE TO METHYL NONANOATE - EFFECT OF VARYING OPERATING CONDITIONS[a]

| EX. | [Sn]/[Pd] MOLE RATIO | [1-OCTENE]/[Pd] MOLE RATIO | TIME (hr) | TEMP. (°C) | CO PRESSURE(PSIG) | METHYL $C_9$ ACID ESTER[b] SELECTIVITY(%)[c] | YIELD(MOLE%)[d] |
|---|---|---|---|---|---|---|---|
| 23 | 100 | 140 | 8 | 80 | 2000 | 91.0 | 24 |
| 24 | 45 | 106 | 8 | 95 | 2000 | 79.8 | 73 |
| 25 | 5 | 46 | 10 | 95 | 2000 | 75.8 | 93 |
| 26 | 10 | 10 | 2 | 75 | 2000 | 82 | 90 |
| 27 | 10 | 500 | 12 | 95 | 2000 | 91.2 | 30 |
| 28 | 10 | 100 | 12 | 25 | 1500 | 90.8 | 10 |
| 29 | 10 | 100 | 2 | 120 | 1500 | 80 | 43 |
| 30 | 10 | 100 | 12 | 80 | 100 | 82 | 10 |

[a]All runs carried out with at least stoichiometric amounts of CO and methanol present with respect to 1-octene charged.
[b]A mixture of methyl nonanoate with some methyl 2-methyloctanoate and methyl 2-ethylheptanoate.
[c]Selectivity to linear methyl nonanoate calculate from total methyl nonanoate/total methyl $C_9$ acid ester.
[d]Yield of total ester based on 1-octene charged.

EXAMPLES 31 TO 34

THE CARBOXYLATION OF 1-OCTENE TO METHYL NONANOATE — CATALYST RECYCLE STUDY — I

Using the general procedure of Example 1A, additional runs were made with a 1-octene, methanol charge mixture and the catalyst system:

$[(C_2H_5)_4N]SnCl_3\text{-}PdCl_2[P(C_6H_5)_3]_2$

However, four(4) different fractions of 1-octene were carboxylated separately in these examples using a single sample of Pd catalyst. Recovery of the product methyl nonanoate after each cycle by an ether extraction technique, and recycle of the palladium catalyst, were carried out as follows:

through 31, using the same procedures and the same 1-octene, methanol charge stocks, the platinum catalyst $[(C_2H_5)_4N]SnCl_3\text{-}PtCl_2[P(C_6H_5)_3]_2$ was tested for catalyst recycle capability. Yields of methyl nonanoate were less than 2% for each of the four catalyst cycles.

EXAMPLES 35 TO 40

THE CARBOXYLATION OF 1-OCTENE TO ETHYL NONANOATE — CATALYST RECYCLE STUDY — II

Using the general procedure of Example 1A, additional carboxylation runs are made with six fractions of 1-octene, ethanol charge mixture, and a single sample of the catalyst $[(C_2H_5)_4N]SnCl_3\text{-}PdCl_2[P(C_6H_5)_3]_2$. Here, however, the product ethyl nonanoate ester is recovered after each cycle by a vacuum distillation technique, and the palladium catalyst recycled as follows:
1. The crude liquid product containing the liquid ester is filtered from the crystalline melt.
2. The crude liquid product of (1) is subject to distillation under reduced pressure (1 cm to 75 cm of mercury) to strip off unreacted octene and ethanol.
3. The partially purified ester is subject to fractional distillation in vacuo (1 to 50 mm of mercury).
4. The recovered melt catalyst from steps (1) and (3) is combined and recycled with additional equimolar, 1-octene, ethanol mixture.

ation reactions for the synthesis of linear fatty acids and esters rom α-olefin stocks.

Among the more important gains over similar types of palladium catalysts, such as $[(C_6H_5)_3P]_2PdCl_2\text{-}SnCl_2$*, used with conventional liquid solvents, are the greater ease in separating the product acids or esters from the reaction medium, the smaller bulk of the reaction mixture, and the greater thermal stability imparted to this type of ligand-stabilized palladium catalyst.

*See U.S. Pat. No. 3,700,706

In order to gain better perspective insofar as the

TABLE 5

CARBOXYLATION OF 1-OCTENE TO ETHYL NONANOATE - CATALYST RECYCLE STUDY - II[a]

| EXAMPLE | CATALYST CYCLE | OCTENE CONVERSION(%) | LIQUID YIELD(%) | ETHYL $C_9$ ACID ESTER[b] SELECTIVITY(%) | YIELD(MOLE %) | ISOLATED ESTER PURITY(%) |
|---|---|---|---|---|---|---|
| 35 | I   | 80 | 78  | 71.0 | 84 | 99 |
| 36 | II  | 80 | 100 | 75.9 | 88 | 99 |
| 37 | III | 70 | 100 | 89.7 | 69 | 99 |
| 38 | IV  | 53 | 96  | 90.0 | 52 | 99 |
| 39 | V   | 32 | 100 | 91.2 | 31 | 99 |
| 40 | VI  | 14 | 100 | 92.0 | 14 | 99 |

[a]Run Conditions: 1500 psig CO; 85°C; [Sn]/[Pd]=10; [1-octene]/[Pd]=63; [ethanol]/[1-octene]=1.0

As can be seen from the results in Table 5, the $PdCl_2[P(C_6H_5)_3]_2$ complex dispersed in $[(C_2H_5)_4N]SnCl_3$ remains active for 1-octene carboxylation over at least six cycles, without the need to modify the catalyst in any way. Once again, the selectivity to linear ethyl nonanoate improves with successive cycling.

EXAMPLES 41 TO 44

THE CARBOXYLATION OF 1-HEXENE TO ETHYL HEPTANOATE CATALYST RECYCLE STUDY - III

Using the general procedure of Example 1A, further carboxylation runs are made with four (4) fractions of 1-hexene, ethanol charge mixture, and a single sample of the catalyst $[(C_2H_5)_4N]SnCl_3\text{-}PdCl_2[P(p\text{-}CH_3.C_6H_4)_3]_2$. The product ethyl heptanoate ester is recovered after each cycle by the vacuum distillation technique described in Example 32.

As can be seen from the results presented in Table 6, the catalyst $[(C_2H_5)_4N]SnCl_3\text{-}PdCl_2[P(p\text{-}CH_3\text{-}C_6H_4)_3]_2$ provides an excellent means for the multiple synthesis of heptanoate esters from 1-hexene.

scope or metes and bounds of the subject invention are concerned, a careful reading of the claims which follows is recommended, in conjunction with the preceding specification.

What is claimed is:

1. A process for preparing linear, carboxylic (fatty) acids and their ester derivatives through the catalytic reaction of alpha-olefins containing from about 3 to about 40 carbon atoms, carbon monoxide and hydroxyl-containing co-reactants by:
   a. admixing each molar equivalent of alpha-olefin to be carboxylated with at least a stoichiometric amount of hydroxyl-containing co-reactant selected from the group consisting of water, alkanols, alkane diols, containing 1 to 12 carbon atoms, chloroalkanols containing 1 to 4 carbon atoms, and at least a catalyst amount of ligand-stabilized palladium(II) halide complex dispersed in quaternary ammonium, phosphonium and arsonium salts of trihalostannate(II) or trihalogermanate(II) selected from the group consisting of:

$[(C_2H_5)_4N][SnCl_3]\text{-}PdCl_2[P(p\text{-}CH_3.C_6H_4)_3]_2$
   $[(C_2H_5)_4N][SnCl_3]\text{-}PdCl_2[P(C_6H_5)_3]_2$

TABLE 6

CARBOXYLATION OF 1-HEXENE TO ETHYL HEPTANOATE - CATALYST RECYCLE - III

| EXAMPLE | CATALYST CYCLE | ETHYL $C_7$ ACID ESTERS SELECTIVITY(%) | YIELD (MOLE %) | ISOLATED ESTER PURITY (%) |
|---|---|---|---|---|
| 41 | I   | 67.3 | 95 | 99 |
| 42 | II  | 71.8 | 94 | 99 |
| 43 | III | 86.6 | 70 | 99 |
| 44 | IV  | 90.8 | 51 | 99 |

As established by the preceding examples and Tables, numerous advantages accrue from the practice of this invention wherein certain empirically derived catalysts consisting of ligand-stabilized palladium(II) complexes dispersed in quaternary ammonium, phosphonium and arsonium salts of trihalostannate(II) and trihalogermanate(II), have been employed in carboxyl- $[ClCH_2(C_6H_5)_3P][SnCl_3]\text{-}PdCl_2[P(C_6H_5)_3]_2$
$[(n\text{-}C_4H_9)_4N][SnCl_3]\text{-}PdCl_2[P(C_6H_5)_3]_2$
$[(C_6H_5)_4As][SnCl_3]\text{-}PdCl_2[P(C_6H_5)_3]_2$
$[(C_7H_{15})_4N][SnCl_3]\text{-}PdCl_2[P(C_6H_5)_3]_2$
$[(C_2H_5)_4N][SnCl_3]\text{-}PdCl_2[P(p\text{-}CH_3O.C_6H_4)_3]_2$
$[(C_2H_5)_4N][SnCl_3]\text{-}PdCl_2[P(CH_3)_2C_6H_5]_2$
$[(C_2H_5)_4N][GeCl_3]\text{-}PdCl_2[P(C_6H_5)_3]_2$
$[(C_2H_5)_4N][GeCl_3]\text{-}PdCl_2[As(C_6H_5)_3]_2$ wherein the molar ratio of quaternary tin(II) or germanium(II) salt to palladium is between 2 to 10 to 1, in a substantially oxygen-free environment, in the present of at least a stoichiometric amount of carbon monoxide with respect to olefin, at superatmospheric pressures of carbon monoxide of at least 100 psig, to form a pressurized reaction mixture;

b. heating said reaction mixture at temperatures ranging from about 25° to 120°C for a time sufficient to substantially carboxylate said alpha-olefin to the corresponding carboxylic (fatty) acid or ester, and c. isolating said carboxylated products prepared therein.

2. The process of claim 1 wherein the reaction mixture contains as the hydroxylated co-reactant water, and the carboxylated product is a linear fatty (carboxylic) acid.

3. The process of claim 1 wherein said catalyst complex is preformed prior to the formation of the reaction mixture.

4. The process of claim 1 wherein said catalyst complex is prepared in situ by adding as separate components the ligand-stabilized palladium halide complex and the quaternary ammonium, phosphonium, and arsonium salt of trihalostannate(II) or trihalogermanate(II).

5. The process of claim 1 in which the alpha-olefin to be carboxylated is 1-octene, the hydroxylated co-reactant is ethanol, and the palladium catalyst complex is $[(C_2H_5)_4N]SnCl_3\text{-}PdCl_2[P(C_6H_5)_3]_2$ and the major linear fatty acid ester product is ethyl nonanoate.

6. A process for preparing linear, carboxylic (fatty) acids and their ester derivatives through the catalytic reaction of alpha-olefins containing from about 3 to about 40 carbon atoms, carbon monoxide and hydroxyl-containing co-reactants by:

a. admixing each molar equivalent of alpha-olefin to be carboxylated with at least a stoichiometric amount of hydroxyl-containing co-reactant selected from the group consisting of water, alkanols, alkane diols, containing 1 to 12 carbon atoms, chloroalkanols containing 1 to 4 carbon atoms, and at least a catalytic amount of ligand-stabilized palladium(II) halide complex dispersed in quaternary ammonium, phosphonium and arsonium salts of trihalostannate(II) or trihalogermanate(II) selected from the group consisting of:

$[(C_2H_5)_4As][SnCl_3]\text{-}PdCl_2[P(C_6H_5)_3]_2$
$[(C_2H_5)_4N][GeCl_3]\text{-}PdCl_2[As(C_6H_5)_3]_2$, and
$[(C_2H_5)_4N][SnCl_3]\text{-}PdCl_2[As(C_6H_5)_3]_2$ wherein the molar ratio of quaternary tin(II) or germanium(II) salt to palladium is between 2 to 10 to 1, in a substantially oxygen-free environment, in the presence of at least a stoichiometric amount of carbon monoxide with respect to olefin, at superatmospheric pressures of carbon monoxide of at least 100 psig, to form a pressurized reaction mixture;

b. heating said reaction mixture at temperatures ranging from about 25° to 120°C for a time sufficient to substantially carboxylate said alpha-olefin to the corresponding carboxylic (fatty) acid or ester, and c. isolating said carboxylated products prepared therein.

* * * * *

UNITED STATES PATENT AND TRADEMARK OFFICE
CERTIFICATE OF CORRECTION

PATENT NO. : 3,968,133
DATED : July 6, 1976
INVENTOR(S) : John F. Knifton

It is certified that error appears in the above-identified patent and that said Letters Patent are hereby corrected as shown below:

Column 2, line 48: "sufficient" should read --insufficient--

Column 4, line 46: "environmenrt" should read --environment--

Column 6, line 7; "(60)" should read --($\alpha$)--

Column 8, line 19: "nonandate" should read --nonanoate--

Column 9, line 33: "transistion" should read --transition--

Column 14, line 42: "catalyst" should read --catalytic--

Column 15, line 3: "present" should be --presence--

Signed and Sealed this twelfth Day of July 1977

[SEAL]

Attest:

RUTH C. MASON
Attesting Officer

C. MARSHALL DANN
Commissioner of Patents and Trademarks